United States Patent
Boon et al.

(10) Patent No.: US 9,822,048 B2
(45) Date of Patent: Nov. 21, 2017

(54) METHOD OF EXTENDING BIOMASS CONVERSION CATALYST LIFE

(71) Applicant: SHELL OIL COMPANY, Houston, TX (US)

(72) Inventors: Andries Quirin Maria Boon, Houston, TX (US); Joseph Broun Powell, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/378,099

(22) Filed: Dec. 14, 2016

(65) Prior Publication Data

US 2017/0166502 A1    Jun. 15, 2017

Related U.S. Application Data

(60) Provisional application No. 62/266,736, filed on Dec. 14, 2015.

(51) Int. Cl.

| | | |
|---|---|---|
| C07C 29/00 | (2006.01) | |
| B01J 37/00 | (2006.01) | |
| C10G 3/00 | (2006.01) | |
| C07C 29/145 | (2006.01) | |
| B01J 37/20 | (2006.01) | |
| C10G 1/06 | (2006.01) | |
| B01J 23/755 | (2006.01) | |
| B01J 23/882 | (2006.01) | |

(52) U.S. Cl.
CPC ............. *C07C 29/145* (2013.01); *B01J 37/20* (2013.01); *C10G 1/065* (2013.01); *C10G 3/00* (2013.01); *B01J 23/755* (2013.01); *B01J 23/882* (2013.01)

(58) Field of Classification Search
CPC ........... C07C 29/145; B01J 37/20; C10G 3/00
USPC ........................................................ 568/881
See application file for complete search history.

(56) References Cited

U.S. PATENT DOCUMENTS

| | | | |
|---|---|---|---|
| 9,102,584 B2 * | 8/2015 | Powell | .................. B01J 21/063 |
| 9,353,478 B2 | 5/2016 | Powell et al. | |
| 9,458,247 B2 | 10/2016 | Powell et al. | |
| 2010/0236988 A1 | 9/2010 | Gabrielov et al. | |
| 2012/0317872 A1 | 12/2012 | Powell et al. | |
| 2012/0317873 A1 | 12/2012 | Johnson et al. | |
| 2013/0109896 A1 | 5/2013 | Powell et al. | |
| 2013/0152457 A1 | 6/2013 | Powell et al. | |
| 2013/0152458 A1 | 6/2013 | Powell et al. | |
| 2014/0005444 A1 | 1/2014 | Komplin et al. | |
| 2014/0005445 A1 | 1/2014 | Komplin et al. | |
| 2014/0117275 A1 | 5/2014 | Powell et al. | |
| 2014/0117276 A1 | 5/2014 | Powell et al. | |
| 2014/0117277 A1 | 5/2014 | Powell et al. | |
| 2014/0121419 A1 | 5/2014 | Powell et al. | |
| 2014/0166221 A1 | 6/2014 | Powell et al. | |
| 2014/0174432 A1 | 6/2014 | Powell | |
| 2014/0174433 A1 | 6/2014 | Powell | |
| 2015/0166681 A1 | 6/2015 | Chheda et al. | |
| 2015/0166682 A1 | 6/2015 | Powell et al. | |
| 2015/0167235 A1 | 6/2015 | Powell et al. | |
| 2015/0167236 A1 | 6/2015 | Powell et al. | |
| 2015/0167237 A1 | 6/2015 | Powell et al. | |
| 2015/0167238 A1 | 6/2015 | Powell et al. | |
| 2015/0167239 A1 | 6/2015 | Powell et al. | |
| 2015/0167240 A1 | 6/2015 | Powell et al. | |
| 2015/0167241 A1 | 6/2015 | Powell et al. | |
| 2015/0184081 A1 | 7/2015 | Powell et al. | |

OTHER PUBLICATIONS

U.S. Appl. No. 62/186,941, filed Jun. 30, 2015.
U.S. Appl. No. 62/186,902, filed Jun. 30, 2015.
U.S. Appl. No. 62/186,919, filed Jun. 30, 2015.
U.S. Appl. No. 62/186,960, filed Jun. 30, 2015.

* cited by examiner

*Primary Examiner* — Sikarl Witherspoon

(57) ABSTRACT

A method of extending the catalyst life of a hydrogenolysis catalyst activity in the presence of biomass and aqueous solution is described. Lignocellulosic biomass solids and aqueous solution is provided to in a hydrothermal digestion unit in the presence of a digestive solvent, and a supported hydrogenolysis catalyst containing (a) sulfur, (b) Mo or W, and (c) Co, Ni or mixture thereof, incorporated into a solid metal oxide support. The lignocellulosic biomass solids in the hydrothermal digestion unit is heated to a temperature in the range of 180° C. to less than 300° C. in the presence of digestive solvent, hydrogen, and in the range of 0.15 wt. % to 12.5 wt. %, based on catalyst, of $H_2S$ or $H_2S$ source at least partially soluble in aqueous solution, and the supported hydrogenolysis catalyst forming a product solution containing plurality of oxygenated hydrocarbons, the hydrothermal digestion unit maintaining protective sulfur concentration.

18 Claims, 1 Drawing Sheet

METHOD OF EXTENDING BIOMASS CONVERSION CATALYST LIFE

The present application claims the benefit of U.S. Provisional Application Ser. No. 62/266,736 filed 14 Dec. 2015, the entire disclosure of which is hereby incorporated by reference.

FIELD OF THE INVENTION

The invention relates to conversion of biomass to hydrocarbons. More specifically, the invention relates to a method of extending catalyst life of a biomass conversion catalyst.

BACKGROUND OF THE INVENTION

A significant amount of attention has been placed on developing new technologies for providing energy from resources other than fossil fuels. Biomass is a resource that shows promise as a fossil fuel alternative. As opposed to fossil fuel, biomass is also renewable.

Biomass may be useful as a source of renewable fuels. One type of biomass is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose. Hemicellulose and pectin are typically found in abundance, but cellulose is the predominant polysaccharide and the most abundant source of carbohydrates. However, production of fuel from cellulose poses a difficult technical problem. Some of the factors for this difficulty are the physical density of lignocelluloses (like wood) that can make penetration of the biomass structure of lignocelluloses with chemicals difficult and the chemical complexity of lignocelluloses that lead to difficulty in breaking down the long chain polymeric structure of cellulose into carbohydrates that can be used to produce fuel. Another factor for this difficulty is the nitrogen compounds and sulfur compounds contained in the biomass. The nitrogen and sulfur compounds contained in the biomass can poison catalysts used in subsequent processing.

Most transportation vehicles require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier.

Currently, bio-based feedstocks such as biomass provide the only renewable alternative for liquid transportation fuel. Unfortunately, the progress in developing new technologies for producing liquid biofuels has been slow in developing, especially for liquid fuel products that fit within the current infrastructure. Although a variety of fuels can be produced from biomass resources, such as ethanol, methanol, and vegetable oil, and gaseous fuels, such as hydrogen and methane, these fuels require either new distribution technologies and/or combustion technologies appropriate for their characteristics. The production of some of these fuels also tends to be expensive and raise questions with respect to their net carbon savings. There is a need to directly process biomass into liquid fuels, amenable to existing infrastructure.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). Further, it is a challenge to minimize generation of waste products that may require treating before disposal and/or catalyst deactivation by poisons.

SUMMARY OF THE INVENTION

It was found that a sulfided hydrogenolysis catalyst containing (a) sulfur, (b) Mo or W, and (c) Co, Ni or mixture thereof, incorporated into a solid metal oxide support was tolerant to certain catalyst poison such as sulfur and nitrogen as described in US20120317872. However, it has been found that such catalyst loose catalytic activity in the presence of water in the reaction mixtures with biomass. Applicants have found that by maintaining a partial pressure of $H_2S$ in the hydrothermal digestion unit, the catalyst life can be extended.

A method of extending the catalyst life of a hydrogenolysis catalyst activity in the presence of biomass and aqueous solution is provided, comprising: (i) providing lignocellulosic biomass solids and aqueous solution in a hydrothermal digestion unit in the presence of a digestive solvent, and a supported hydrogenolysis catalyst containing (a) sulfur, (b) Mo or W, and (c) Co, Ni or mixture thereof, incorporated into a solid metal oxide support; (ii) heating the lignocellulosic biomass solids in the hydrothermal digestion unit to a temperature in the range of 180° C. to less than 300° C. in the presence of digestive solvent, hydrogen, and in the range of 0.15 wt. % to 12.5 wt. %, based on catalyst, of $H_2S$ or $H_2S$ source at least partially soluble in aqueous solution, and the supported hydrogenolysis catalyst thereby forming a product solution containing plurality of oxygenated hydrocarbons, said hydrothermal digestion unit maintaining protective sulfur concentration.

The features and advantages of the invention will be apparent to those skilled in the art. While numerous changes may be made by those skilled in the art, such changes are within the spirit of the invention.

BRIEF DESCRIPTION OF THE DRAWING

The drawings illustrate certain aspects of some of the embodiments of the invention, and should not be used to limit or define the invention.

DETAILED DESCRIPTION OF THE INVENTION

Figure 1:
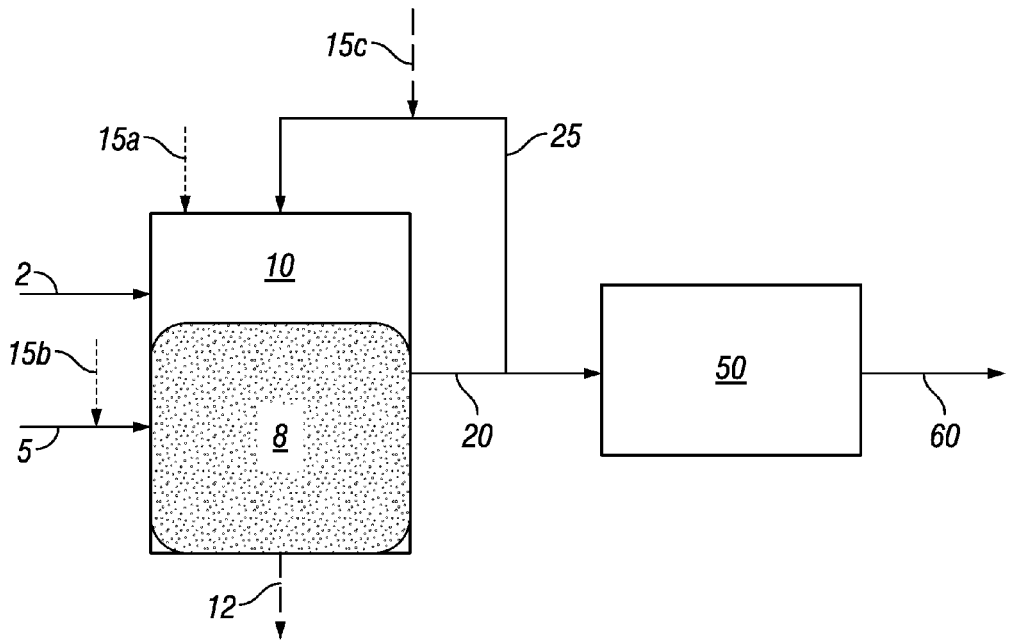
FIG. 1 is a schematic illustration of an embodiment of a process of this invention.

In an embodiment, the invention relates to a method of extending the catalyst life of the activity of a supported hydrogenolysis catalyst containing (a) sulfur, (b) Mo or W, and (c) Co, Ni or mixture thereof, incorporated into a solid metal oxide support in the presence of biomass and aqueous solution. It has been found that water in the aqueous system with biomass deactivates the hydrogenolysis activity of such catalyst rapidly under reaction conditions. However, it was found that such catalyst activity under reaction conditions may be extended (extending catalyst life) by contacting the lignocellulosic biomass solids under reaction conditions in the hydrothermal digestion unit in the presence of $H_2S$ or $H_2S$ source at least partially soluble in aqueous solution, in a range of 0.15 wt. % to 12.5 wt. %, based on catalyst, maintaining protective sulfur concentration (that maybe measured depending on the unit conditions as $H_2S$ partial pressure) in the hydrothermal digestion unit.

The higher hydrocarbons produced are useful in forming transportation fuels, such as synthetic gasoline, diesel, and jet fuels. As used herein, the term "higher hydrocarbons" refers to hydrocarbons having an oxygen to carbon ratio less than the oxygen to carbon ratio of at least one component of the biomass feedstock. The higher hydrocarbon predominantly contains C4 to C30 hydrocarbons, more preferably C6 to C18 hydrocarbons. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (i.e., oxygen sulfur, phosphorus, or nitrogen) and thus the term "hydrocarbon" may also include substituted hydrocarbons. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. Further the process should maximize product yield while minimizing waste products. These basic requirements lead to a number of secondary issues that collectively present an immense engineering challenge that has not been solved heretofore.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars).

Various illustrative embodiments will be further described with reference to FIG. 1. In FIG. 1 show illustrative embodiments of biomass conversion process to hydrocarbon.

Any suitable (e.g., inexpensive and/or readily available) type of lignocellulosic biomass can be used as a solid biomass. Suitable lignocellulosic biomass can be, for example, selected from, but not limited to, wood, forestry residues, agricultural residues, herbaceous material, municipal solid wastes, pulp and paper mill residues, and combinations thereof. Thus, in some embodiments, the biomass can comprise, for example, corn stover, straw, bagasse, miscanthus, sorghum residue, switch grass, duckweed, bamboo, water hyacinth, hardwood, hardwood chips, hardwood pulp, softwood, softwood chips, softwood pulp, and/or combination of these feedstocks. The biomass can be chosen based upon a consideration such as, but not limited to, cellulose and/or hemicelluloses content, lignin content, growing time/season, growing location/transportation cost, growing costs, harvesting costs and the like.

Prior to processing, the untreated biomass can be reduced in size (e.g., chopping, crushing or debarking) to a convenient size and certain quality that aids in moving the biomass or mixing and impregnating the chemicals from digestive solvent. Thus, in some embodiments, providing biomass can comprise harvesting a lignocelluloses-containing plant such as, for example, a hardwood or softwood tree. The tree can be subjected to debarking, chopping to wood chips of desirable thickness, and washing to remove any residual soil, dirt and the like.

The biomass solids are introduced in to a vessel from an inlet. The vessel can be in any shape that include, for example, vertical, horizontal, incline, and may include bends, curves or u shape. The vessel will further have at least one inlet and at least one outlet.

The biomass may optionally be washed with an acidic or basic solution to remove metal species and its corresponding anions such as Mg, Ca, Na, K Fe, Mn, Cl, $SO_4$, $PO_4$, $NO_3$ that are detrimental to catalysts or equipment used in the hydrothermal hydrocatalytic treatment from the biomass. Such treatment disclosed in commonly owned co-pending U.S. Patent Application Publication Nos. US20150166681, US20150167236, US20150166682, US20150167241, US20150167238, US20150167235, US20150167240, US20150167237, US20150167239, and US20150184081, which disclosures are hereby incorporated by reference in its entirety.

At least a portion of the optionally treated cellulosic biomass solids is provided to a digestion and/or reaction zone (collectively referred to as "hydrothermal hydrocatalytic reaction zone", for example represented as 10 in FIG. 1) for digesting and hydrodeoxygenating. This zone may be conducted in a single step or in multiple steps or vessels as described below.

For the hydrothermal catalytic reaction zone, the zone may have one or more vessels. In one embodiment in the digestion/reaction zone hydrolysis and hydrothermal hydrocatalytic reaction of the treated biomass is carried out in one or more vessels. These vessels may be digesters or reactors or combination thereof including a combination hydrothermal hydrocatalytic digestion unit.

In some embodiments, lignocellulosic biomass (solids), 2, being continuously or semi-continuously added to the hydrothermal digestion unit or hydrothermal hydrocatalytic digestion unit may be pressurized before being added to the unit, particularly when the hydrothermal (hydrocatalytic) digestion unit is in a pressurized state. Aqueous solution (or water) may be added with the biomass solids or separately. Pressurization of the cellulosic biomass solids from atmospheric pressure to a pressurized state may take place in one or more pressurization zones before addition of the cellulosic biomass solids to the hydrothermal (hydrocatalytic) digestion unit. Suitable pressurization zones that may be used for pressurizing and introducing lignocellulosic biomass to a pressurized hydrothermal digestion unit or hydrothermal hydrocatalytic digestion unit are described in more detail in commonly owned United States Patent Application Publication Nos. US20130152457 and US20130152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner. The digestion and the hydrothermal hydrocatalytic reaction in the hydrothermal catalytic reaction zone (or digestion reaction zone) may be conducted separately, partially combined, or in situ.

The biomass solid is hydrothermally digested and hydrodeoxygenated in a liquid-phase digestive solvent, in the presence of hydrogen and a hydrogenolysis catalyst described here in a hydrothermal digestion unit, at a temperature in the range of from 110° C. to less than 300° C. at a pressure in a range of from 20 bar to 200 bar to form stable oxygenated hydrocarbon intermediate product mixtures (plurality of oxygenated hydrocarbons). The stable oxygenated hydrocarbon intermediate product mixture, in general, has a viscosity of less than 100 centipoise (at 50° C.), a diol content, less than 2 wt. % of sugar, and less than 2 wt. % organic acid based on acetic acid equivalent, and at least 60% of carbon in formed product exists in molecules having 10 carbon atoms or less. The catalyst zone is represented as 8 in FIG. 1 where the hydrogenolysis catalyst may be present as fixed bed or slurry catalyst in the zone.

In the process, the lignocellulosic biomass solids in the hydrothermal digestion unit is heated to a temperature in the range of 180° C. to less than 300° C. in the presence of digestive solvent, hydrogen, and in the range of 0.15 wt. % to 12.5 wt. %, preferably 0.15 to 10 wt. %, more preferably 0.15 to 5 wt. %, based on catalyst, of $H_2S$ or $H_2S$ source at least partially soluble in aqueous solution, and the supported hydrogenolysis catalyst thereby forming a product solution containing plurality of oxygenated hydrocarbons, where the hydrothermal digestion unit maintains $H_2S$ partial pressure. Preferably, the residence time of the hydrothermal digestion unit (Vol/Feed) is in the range of 0.5 to 20 h.

It was found that by adding $H_2S$ and/or $H_2S$ source at least partially soluble in aqueous solution that can provide $H_2S$ partial pressure to the hydrothermal digestion unit, extends the catalyst activity life of the hyrogenalysis catalyst described herein. Examples of $H_2S$ source at least partially soluble in aqueous solution includes, for example, $SO_2$, dimethylsulfoxide (DMSO), cysteine, dimethylsulfide, dimethyldisulfide, N-butylmercaptan, tertiarybutyl polysulfide, sodium sulfide, sodium thiosulfate and Sulfrzol. The $H_2S$ and/or $H_2S$ source provide access to sulfur that is of fully oxidized and can be incorporated into the metal catalyst. The hydrothermal digestion unit should maintain a protective sulfur concentration to maintain catalyst activity. By the term "protective sulfur concentration" means concentration of sulfur compounds ("protective sulfur") that includes $H_2S$ and/or $H_2S$ source and other reduced forms of sulfur compounds derived therefrom, but does not include sulfur incorporated on the catalyst. It is recognized that the system may contain sulfates or other fully oxidized species that do not contribute to the sulfur concentration.

Depending on the $H_2S$ source, it may be added in any number of locations and stream upstream of the hydrothermal digestion unit or directly to the hydrothermal digestion unit. Some of the locations are depicted in alternatives on FIG. 1 as various position of inlet 15 (a, b, c, etc.). For example, when $H_2S$ and/or a gaseous $H_2S$ source such as for example $SO_2$ is added, they may be added to Hydrogen gas stream (for example 5 in FIG. 1) inlet. In another embodiment, if at least a portion of the product solution is recycled (for example 25 in FIG. 1) to the to the hydrothermal digestion unit via a liquid recycle stream, such $H_2S$ source may be added to such recycle stream. For example, dimethyl sulfoxide, dimethyl sulfide, dimethyldisulfide, n-butylmercaptan, teriarybutylpolysulfide, sodium sulfide, sodium thiosulfate, and/or cysteine may be added to the liquid recycle stream. Any non-fully oxidized sulfur compounds such as, for example, those listed above may be used. "$H_2S$ Source" means that the sulfur compound is capable of generating $H_2S$ in the system, but may not necessary generating $H_2S$. For example, under basic conditions the sulfur compound may generate HS— and/or $S_2$—.

Further monitoring the $H_2S$ level in the gas phase in the hydrothermal digestion unit may be desirable and adjusting the addition of $H_2S$ or $H_2S$ source to maintain said $H_2S$ partial pressure or protective sulfur concentration. Such monitoring may be conducted with $H_2S$ monitors or sensors or measuring devices available commercially (collectively referred to as "$H_2S$ monitoring device"). Which is in flow communication with the hydrothermal digestion unit. Adjustment may be conducted manually or a processing device communicatively coupled to $H_2S$ monitoring device and the control device to control the addition of the $H_2S$ or $H_2S$ source, where the processing device is configured to actuate the control device if the level of $H_2S$ exceeds or falls below a threshold value in the hydrothermal digestion unit.

The $H_2S$ or the source of $H_2S$ (referred collectively as "S component") may further be recycled via gas or liquid phase recycle. For example, gas phase recycle may be recycled along with $H_2$ gas recycle back to the hydrothermal digestion unit. In another example, the liquid phase recycle may be recycled through a solvent recycle or any other liquid stream recycled to the hydrothermal digestion unit. The source of $H_2S$ or its derivative or protective sulfur may also be recycled via liquid phase recycle to the hydrothermal digestion unit.

In some embodiments, the digestion rate of cellulosic biomass solids may be accelerated in the presence of a liquid phase containing a digestion solvent. In some instances, the liquid phase may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures. One approach for addressing the degradation of soluble carbohydrates during hydrothermal digestion is to conduct an in situ catalytic reduction reaction process so as to convert the soluble carbohydrates into more stable compounds as soon as possible after their formation.

In certain embodiments, a slurry catalyst of the hydrogenolysis catalyst may be effectively distributed from the bottom of a charge of cellulosic biomass solids to the top using upwardly directed fluid flow to fluidize and upwardly convey slurry catalyst particulates into the interstitial spaces within the charge for adequate catalyst distribution within the digesting cellulosic biomass solids. Suitable techniques for using fluid flow to distribute a slurry catalyst within cellulosic biomass solids in such a manner are described in commonly owned United States Patent Application Publication Nos. US20140005445 and US20140005444, which are incorporated herein by reference in its entirety. In addition to affecting distribution of the slurry catalyst, upwardly directed fluid flow may promote expansion of the cellulosic biomass solids and disfavor gravity-induced compaction that occurs during their addition and digestion, particularly as the digestion process proceeds and their structural integrity decreases. Methods of effectively distributing molecular hydrogen within cellulosic biomass solids during hydrothermal digestion is further described in commonly owned United States Patent Application Publication Nos. US20140174433 and US20140174432, which are incorporated herein by reference in its entirety.

In another embodiment the hydrothermal hydrocatalytic digestion unit may be configured as disclosed in a co-pending US Application Publication No. US20140117276 which disclosure is hereby incorporated by reference. In the digestion zone, the size-reduced biomass is contacted with the digestive solvent where the digestion reaction takes place. The digestive solvent must be effective to digest lignins. The digestive solvent is typically a solvent mixture having a boiling point of at least 40° C.

In some embodiments, at least a portion of oxygenated hydrocarbons produced in the hydrothermal hydrocatalytic reaction zone are recycled within the process and system to at least, in part, form the in situ generated solvent, which is used in the biomass digestion process. Further, by controlling the rate of digestion of biomass to lower molecular weight fragments in the hydrothermal hydrocatalytic reaction (e.g., hydrogenolysis process), hydrogenation reactions can be conducted along with the hydrogenolysis reaction at temperatures ranging of from 110° C., preferably from about 150° C. to less than 300° C., most preferably from about 240° C. to about 270° C. As a result the fuel forming potential of the biomass feedstock fed to the process can be increased.

In various embodiments, the fluid phase digestion medium (liquid digestive solvent) in which the hydrothermal digestion and catalytic reduction reaction (in the hydrothermal hydrocatalytic reaction zone) are conducted, may comprise an organic solvent and water. The liquid digestive solvent mixture may have a normal boiling point (i.e., at atmospheric pressure) of at least 40° C., preferably at least 60° C., more preferably at least 80° C. Although any organic solvent that contains some oxygen atoms may be used as a digestion solvent, particularly advantageous organic solvents are those that can be directly converted into fuel blends and other materials and hence do not require extensive separation from intermediate streams used in the production of biofuels, or co-product streams used as fuel or separated and processed as chemical products. That is, particularly advantageous organic solvents are those that may be co-processed along with the alcoholic or oxygenated components during downstream processing reactions into fuel blends and other materials. Suitable organic solvents in this regard may include, for example, ethanol, ethylene glycol, propylene glycol, glycerol, phenolics and any combination thereof. In situ generated organic solvents are particularly desirable in this regard.

In some embodiments, the liquid phase digestive solvent may comprise between about 1% water and about 99% water. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the liquid phase digestive solvent may comprise about 90% or less water by weight. In other embodiments, the fluid phase digestion medium may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

Hydrogenolysis catalysts suitable for activating molecular hydrogen and buffers suitable for use with such catalysts are described in commonly owned United States Patent Application Publication Nos. US2012/0317872, US2013/0109896, US2012/0317873, and US20140166221, each of which is incorporated herein by reference in its entirety. Sulfiding may take place by treating the catalyst with hydrogen sulfide or an alternative sulfiding agent, optionally while the catalyst is disposed on a solid support. Typically, these sulfiding takes place prior to catalyst activation and reaction. Illustrative techniques for catalyst sulfiding that may be used in conjunction with the methods described herein are described in United States Patent Application Publication No. US2010/0236988 and incorporated herein by reference in its entirety. The pH buffering agent, may be suitable be an inorganic salt, particularly alkali salts such as, for example, potassium hydroxide, sodium hydroxide, and potassium carbonate or ammonia.

In various embodiments, slurry catalysts used in conjunction with the methods described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein.

As described above, one or more liquid phases may be present when digesting cellulosic biomass solids. Particularly when cellulosic biomass solids are fed continuously or semi-continuously to the hydrothermal (hydrocatalytic) digestion unit, digestion of the cellulosic biomass solids may produce multiple liquid phases in the hydrothermal digestion unit. The liquid phases may be immiscible with one another, or they may be at least partially miscible with one another. In some embodiments, the one or more liquid phases may comprise a phenolics liquid phase comprising lignin or a product formed therefrom, an aqueous phase comprising the alcoholic component, a light organics phase, or any combination thereof. The alcoholic component being produced from the cellulosic biomass solids may be partitioned between the one or more liquid phases, or the alcoholic component may be located substantially in a single liquid phase. For example, the alcoholic component being produced from the cellulosic biomass solids may be located predominantly in an aqueous phase (e.g., an aqueous phase digestion solvent), although minor amounts of the alcoholic component may be partitioned to the phenolics liquid phase or a light organics phase. In various embodiments, the slurry catalyst may accumulate in the phenolics liquid phase as it forms, thereby complicating the return of the slurry catalyst to the cellulosic biomass solids in the manner described above. Alternative configurations for distributing slurry catalyst particulates in the cellulosic biomass solids when excessive catalyst accumulation in the phenolics liquid phase has occurred are described hereinafter.

Accumulation of the slurry catalyst in the phenolics liquid phase may, in some embodiments, be addressed by conveying this phase and the accumulated slurry catalyst therein to the same location where a fluid phase digestion medium is being contacted with cellulosic biomass solids. The fluid phase digestion medium and the phenolics liquid phase may be conveyed to the cellulosic biomass solids together or separately. Thusly, either the fluid phase digestion medium and/or the phenolics liquid phase may motively return the slurry catalyst back to the cellulosic biomass solids such that continued stabilization of soluble carbohydrates may take place. In some embodiments, at least a portion of the lignin in the phenolics liquid phase may be depolymerized before or while conveying the phenolics liquid phase for redistribution of the slurry catalyst. At least partial depolymerization of the lignin in the phenolics liquid phase may reduce the viscosity of this phase and make it easier to convey. Lignin depolymerization may take place chemically by hydrolyzing the lignin (e.g., with a base) or thermally by heating the lignin to a temperature of at least about 250° C. in the presence of molecular hydrogen and the slurry catalyst. Further details regarding lignin depolymerization and the use of viscosity monitoring as a means of process control are described in commonly owned United States Patent Application Publication No. US20140117275 which disclosure is incorporated herein by reference in its entirety.

In some embodiments, a phenolics liquid phase formed from the cellulosic biomass solids may be further processed. Processing of the phenolics liquid phase may facilitate the catalytic reduction reaction being performed to stabilize soluble carbohydrates. In addition, further processing of the phenolics liquid phase may be coupled with the production of glycols or dried monohydric alcohols for feeding to a condensation catalyst. Moreover, further processing of the phenolics liquid phase may produce methanol and phenolic compounds from degradation of the lignin present in the cellulosic biomass solids, thereby increasing the overall weight percentage of the cellulosic biomass solids that may be transformed into useful materials. Finally, further processing of the phenolics liquid phase may improve the lifetime of the slurry catalyst.

Various techniques for processing a phenolics liquid phase produced from cellulosic biomass solids are described in commonly owned United States Patent Application Publication Nos. US20140121419, US20140117277, which disclosures are incorporated herein by reference in its entirety. As described therein, in some embodiments, the viscosity of the phenolics liquid phase may be reduced in order to facilitate conveyance or handling of the phenolics liquid phase. As further described therein, deviscosification of the phenolics liquid phase may take place by chemically hydrolyzing the lignin and/or heating the phenolics liquid phase in the presence of molecular hydrogen (i.e., hydrotreating) to depolymerize at least a portion of the lignin present therein in the presence of accumulated slurry catalyst. Deviscosification of the phenolics liquid phase may take place before or after separation of the phenolics liquid phase from one or more of the other liquid phases present, and thermal deviscosification may be coupled to the reaction or series of reactions used to produce the alcoholic component from the cellulosic biomass solids. Moreover, after deviscosification of the phenolics liquid phase, the slurry catalyst may be removed therefrom.

The catalyst may then be regenerated, returned to the cellulosic biomass solids, or any combination thereof. In some embodiments, heating of the cellulosic biomass solids and the fluid phase digestion medium (liquid digestive solvent) to form soluble carbohydrates and a phenolics liquid phase may take place while the cellulosic biomass solids are in a pressurized state. As used herein, the term "pressurized state" refers to a pressure that is greater than atmospheric pressure (1 bar). Heating a fluid phase digestion medium in a pressurized state may allow the normal boiling point of the digestion solvent to be exceeded, thereby allowing the rate of hydrothermal digestion to be increased relative to lower temperature digestion processes. In some embodiments, heating the cellulosic biomass solids and the fluid phase digestion medium may take place at a pressure of at least about 30 bar. In some embodiments, heating the cellulosic biomass solids and the fluid phase digestion medium may take place at a pressure of at least about 60 bar, or at a pressure of at least about 90 bar. In some embodiments, heating the cellulosic biomass solids and the fluid phase digestion medium may take place at a pressure ranging between about 30 bar and about 430 bar. In some embodiments, heating the cellulosic biomass solids and the fluid phase digestion medium may take place at a pressure ranging between about 50 bar and about 330 bar, or at a pressure ranging between about 70 bar and about 130 bar, or at a pressure ranging between about 30 bar and about 130 bar.

The digestion and hydrodeoxygenation of the biomass solid described above, produces a stable oxygenated hydrocarbon intermediate product, (for example, 20 in FIG. 1) that have a viscosity of less than 100 centipoise (at 50° C.), preferably less than 40 centipoise, containing plurality of oxygenated hydrocarbon (may contain diol and preferably less than 2 wt % of sugar, and less than 2 wt % acid based on acetic acid equivalent, based on the total stream composition) and at least 60% of carbon exists in molecules having 9 carbon atoms or less. By the term "stable", the product is stable enough to be stored for at least 30 days where the viscosity does not change more than 50% and the main components (top 10 percent based on mass basis) does not change in concentration by more than 10%.

Optionally, the stable oxygenated hydrocarbon intermediate product (plurality of oxygenated hydrocarbons) can be vaporized to allow ash separation from the liquid product (Optional separation of ash for example as 12 in FIG. 1). The vaporized stable oxygenated hydrocarbon can then be provided to the further conversion zone which includes condensation (for example 50 in FIG. 1) described below.

Optionally in such conversion zone, at least a portion of the stable oxygenated hydrocarbon intermediate product may be contacted, in a diol conversion zone, with an acidic amorphous silica alumina catalyst at a temperature in the range from 300° C. to 400° C., preferably 325° C. to 375° C., thereby producing monooxygentaed stream as described in commonly owned U.S. Patent Applications 62/186941, 62/186902, 62/186919, 62/186960, all filed on Jun. 30, 2015, each of which is incorporated herein by reference in its entirety. The temperature and pressure is at a range that optimizes diol conversion while minimizing coke formation (by oligomerization or condensation reactions). The pressure range may be from ambient pressure (atmospheric) to slight partial pressure, for example, total pressure of up to about 200 psi. The reaction typically converts at least 25%, preferably at least 50%, most preferably at least 75% of diols initially present. Typically, the weight hourly space velocity is in the range of 0.2 to 5 for the monooxygenate formation step. Solid acid amorphous silica-alumina catalyst is available commercially, for example, from Criterion Catalyst Co., such as X-600 catalyst series, X-503 catalyst, X-801 catalyst or from CRI Catalyst Company such as KL-7122 catalyst. The monooxygenated stream can be optionally be condensed (in this instance referred to liquid condensation without chemical transformation) in a cooling zone, to liquid producing an aqueous phase and an organic phase. The monooxygenated stream optionally can be phase separated into an aqueous phase and an organic phase upon condensation, thus allowing the aqueous phase containing water and a residual amount of unconverted monooxygenated compounds and diols of carbon number less than four, to be readily removed from the organic phase enriched in monooxygenated organic compounds greater than carbon number four, and phenolic compounds. Optionally, at least a (first) portion of the organic phase can optionally be recycled to the hydrothermal catalytic reaction zone (digestion and hydrodeoxygenation) as a portion of the digestive solvent.

As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. The term "condensation catalyst" will refer to a catalyst that facilitates, causes or accelerates such chemical transformation.

In the further processing zone 50, at least a portion of the plurality of oxygenated hydrocarbon and/or organic phase containing the monooxygenates or the monooxygenate-containing is contacted with a solid acid condensation catalyst separately, for example, as shown in FIG. 1 at a temperature in the range from 275° C. to about 425° C. producing a higher hydrocarbons stream in a condensation reaction zone. In various embodiments, the higher molecular weight compound produced by the condensation reaction may comprise >C4 hydrocarbons. In some or other embodiments, the higher molecular weight compound produced by the condensation reaction may comprise >C6 hydrocarbons. In some embodiments, the higher molecular weight compound produced by the condensation reaction may comprise C4-C30 hydrocarbons. In some embodiments, the higher molecular weight compound produced by the condensation reaction may comprise C6-C30 hydrocarbons. In still other embodiments, the higher molecular weight compound produced by the condensation reaction may comprise C4-C24 hydrocarbons, or C6-C24 hydrocarbons, or C4-C18 hydrocarbons, or C6-C18 hydrocarbons, or C4-C12 hydrocarbons, or C6-C12 hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure. Suitable condensation catalysts include, for example, acid condensation catalysts described in US20140275515 which disclosure is hereby incorporated by reference.

The condensation products 60 may be aromatics-rich hydrocarbon stream when a shape selective condensation catalyst, such as zeolitic catalyst, particularly ZSM-5 catalyst is used in the condensation reaction. To produce aromatics-rich hydrocarbon stream, the acidic ZSM-5 catalyst is contacted at a temperature in the range from 325° C. to about 425° C., preferably 350° C. to 400° C., in the condensation reaction zone, The temperature and pressure is at a range that optimizes condensation reaction while minimizing coke formation. The pressure range may be from ambient pressure (atmospheric) to slight partial pressure, for example, total pressure of up to about 200 psi. The aromatics rich hydrocarbon stream can optionally be washed with aqueous base such as sodium hydroxide, potassium hydroxide to remove residual acids and phenolics (washing zone) to produce biofuel useful as gasoline. These aqueous base typically have a pH of at least 9. The aromatics-rich higher hydrocarbons stream may have at least 50 wt % of aromatics containing hydrocarbon based on the aromatics-rich hydrocarbons stream. The entire organic phase can also be sent to the condensation step. The yield may be greater than 40% of carbons based on biomass carbons due to the increase catalyst uptime (amount of monooxygenated stream passed over the condensation catalyst). Aromatics as defined herein can be quantified by GC-MS analysis and includes any aromatic containing hydrocarbon that contains aromatic rings that are not oxygenated, such as mesytilene, based on molecular content.

The condensation product 60, may be low aromatics, paraffinics-containing stream (aliphatic-rich higher hydrocarbons) when other than shape selective condensation catalyst described above is used in the condensation reaction. The low aromatics, paraffinic-containing stream may further treated in a hydrotreating step (hydrotreating zone) to produce biofuel useful as diesel. This step can be any conventional hydrotreating process. This includes fixed or ebulated bed operations at conventional operating conditions such as temperatures in the range of 250° C. to 450° C., preferably 300° C. to 380° C. Pressures are also conventional such as 20-70 bar of hydrogen. Catalysts used in the hydrotreating step are preferably those employed conventionally, such as mixed cobalt and/or nickel and molybdenum sulfides supported on alumina and mixed nickel and tungsten sulfides supported on alumina or silica. The combined process of this invention will also benefit newly developed catalysts such as those containing ruthenium sulfide and catalysts using novel supports such as silica-aluminas, carbons or other materials. For details on the state of the art in conventional hydrotreating processes, we refer to "Hydrotreating Catalysis-Science and Technology", by H. Topsoe, B. S. Clausen and F. E. Massoth, Springer-Verlag Publishers, Heidelberg, 1996.

At least a portion of the organic phase containing the monooxygenates and/or plurality of oxygenated hydrocarbon may be contacted with a solid acid condensation catalyst under conditions effective to produce low aromatics, paraffinics-containing stream in acid condensation zone to produce an aliphatics and the monooxygenate-containing stream may be contacted with a ZSM-5 catalyst under conditions effective to produce aromatics-rich hydrocarbons stream in acid condensation zone. The aromatics-rich hydrocarbons stream may be base washed in further processing zone and the aliphatic-rich higher hydrocarbons may be hydrotreated in further processing zone.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

While the invention is susceptible to various modifications and alternative forms, specific embodiments thereof are shown by way of examples herein described in detail. It should be understood, that the detailed description is not intended to limit the invention to the particular form disclosed, but on the contrary, the intention is to cover all modifications, equivalents and alternatives falling within the spirit and scope of the present invention as defined by the appended claims. The person skilled in the art will readily understand that, while the invention is illustrated making reference to one or more a specific combinations of features and measures, many of those features and measures are functionally independent from other features and measures such that they can be equally or similarly applied independently in other embodiments or combinations.

To facilitate a better understanding of the present invention, the following examples of preferred embodiments are given. In no way should the following examples be read to limit, or to define, the scope of the invention.

ILLUSTRATIVE EXAMPLES

Examples 1-4: Effect of DMSO Sulfur Blanket 75-ml Parr5000 reactors were was charged with a nominal 25 grams of deionized water, 0.1 grams of potassium carbonate buffer, and 0.2 grams of nickel-oxide promoted cobalt molybdate catalyst (DC-2534 catalyst, containing 1-10% cobalt oxide and molybdenum trioxide (up to 30 wt. %) on alumina, and less than 2% nickel), obtained from Criterion Catalyst & Technologies L.P., and sulfided by the method described in US2010/0236988 Example 5.

For example 1, no sulfur was added to the reactor. For examples 2-4, dimethylsulfoxide (DMSO) was added to provide sulfur concentrations of 15, 37.5, and 60 ppm by weight, based upon the mass of solvent added to the reactors. This provided a mass of sulfur representing 0.2 wt. %, 0.5 wt. %, and 0.8 wt. % relative to the mass of catalyst charged to examples 2-4 respectively. The reactors were pressured with 52 bar hydrogen, and heated for 48 hours at 240° C. After this treatment, the reactors were cooled, depressured, and 0.15 grams of methylethylketone (MEK) were added to assess kinetic activity, by heating to 220° C. for 2 hours under 52 bar of $H_2$, before cooling and sampling for gas chromatographic analysis.

The GC analysis entailed a 60-m×0.32 mm ID DB-5 column of 1 μm thickness, with 50:1 split ratio, 2 ml/min helium flow, and column oven at 40° C. for 8 minutes, followed by ramp to 285° C. at 10° C./min, and a hold time of 53.5 minutes. Acetone was used as diluent for GC analysis of the bottom droplet or globule phase. The injector temperature was set at 250° C., and the detector temperature was set at 300° C. Extent of conversion of MEK to 2-butanol was assessed via GC analysis, and a first-order rate constant calculated from the fractional conversion, and normalized by the weight fraction of catalyst present in solution.

Example 5-7

Cysteine as Sulfur Blanket

The previous experiments were repeated with use of solutions of cysteine as the source of sulfur, in place of DMSO, with sulfur concentrations formulated to match those in the Examples 2-4. For example 6, 250 ppm N basis solvent present was also added as the amino acid alanine, to simulate the large N/S ratio present in biomass feedstocks. This corresponded to 3.1 wt. % N relative to the mass of catalyst charged.

Results for this set of experiments are reported in Table 1. In the absence of added sulfur, a first order rate constant of 10 l/h/wt.-frac catalyst was observed. Observed rates increased with sulfur addition. For a given amount of sulfur added, the rate observed with DMSO was slightly greater than that observed with cysteine, which is an amino acid containing both nitrogen (N) and sulfur (S) functionality. Further addition of alanine in example 6 led to a decrease in kinetic activity relative to a trend in overall increasing activity with increasing sulfur concentration.

Analysis of liquid solutions after hydrothermal exposure showed loss of sulfur to the liquid phase, for the experiment conducted in the absence of sulfur addition.

These results show that a sulfur blanket of 15 ppm sulfur by weight in solution (0.2 wt. % vs. catalyst) as cysteine or DMSO can provide a 5- to 7-fold increase in catalyst activity after 2 days of exposure to hydrothermal stress at 240° C. Increasing the sulfur blanket to 60 ppm by weight in solution (0.8 wt. % vs. catalyst) leads to a further increase in activity despite hydrothermal stress, to values more than 6- to 8-fold in excess of that observed with no sulfur added to the reaction mixture.

These results support the hypothesis that sulfur is lost from the catalyst when exposed to water at temperatures used in hydrothermal digestion of biomass (220-270° C.). This loss leads to a reduction in activity. Addition of a reduced sulfur compound at greater than 15-ppm by weight sulfur in solution (0.2 wt. % vs. catalyst) serves to replace sulfur lost from the catalyst, which provides protection against hydrothermal stress, and improved activity after a period of hydrothermal stress.

TABLE 1

| Ex | S-source | S-ppmw (wt. % vs. catalyst) | k (1/h/wt.) |
|---|---|---|---|
| 1 | DMSO | 0 (0) | 10.00 |
| 2 | DMSO | 15 (0.2%) | 68.37 |
| 3 | DMSO | 37.5 (0.5 wt. %) | 82.94 |
| 4 | DMSO | 60 (0.8 wt. %) | 85.63 |
| 5 | CYSTEINE | 15 (0.2 wt. %) | 52.77 |
| 6 | CYSTEINE | 37.5 (0.5 wt. %) | 39.58 |
| 7 | CYSTEINE | 60 (0.8 wt. %) | 64.38 |

Example 8

Example 4 was repeated with 300 ppm by weight sulfur in solution as DMSO (3.8 wt. % vs. catalyst). A rate constant of 52 l/h/wt. was obtained for the post treatment kinetics test. While activity remained higher than the control with no sulfur added in Example 1, activity was lower than examples 2 through 4, which used lower amounts of sulfur. This result indicates that very high amounts of sulfur lead to a suppression in catalytic activity, despite providing improved protection against deactivation relative to addition of no sulfur.

Examples 9-12: Lower Hydrogen Partial Pressure

Example 5 was repeated at a hydrogen partial pressure of only 16 bar, and amounts of sulfur present as cysteine ranging from zero to 1584 ppm sulfur in solution (19.1) wt. % vs. catalyst. (examples 9-11), while Example 4 was repeated with 1638 ppm sulfur as DMSO in solution (20.5 wt. % vs. catalyst), also at a pressure of 16 bar (example 12). Activity for subsequent hydrogenation was severely diminished in the presence of high concentrations of sulfur.

An overlay of all results (FIG. 2) indicates hydrogenation rates can be improved under the conditions employed via use of sulfur between about 10 and 300 ppm by weight in solution (0.1% to 4 wt. % vs. catalyst) for stabilization of catalyst. Above about 150 ppm (2 wt. % vs. catalyst) and especially above 300 ppm by weight in solution (4 wt. % vs. catalyst), the excess sulfur diminishes catalytic activity, especially at lower hydrogen partial pressures. Above about 1000 ppm S in solution (12% by weight vs. catalyst), suppression by sulfur overcomes the benefits of protecting the catalyst against hydrothermal damage.

Figure 2:
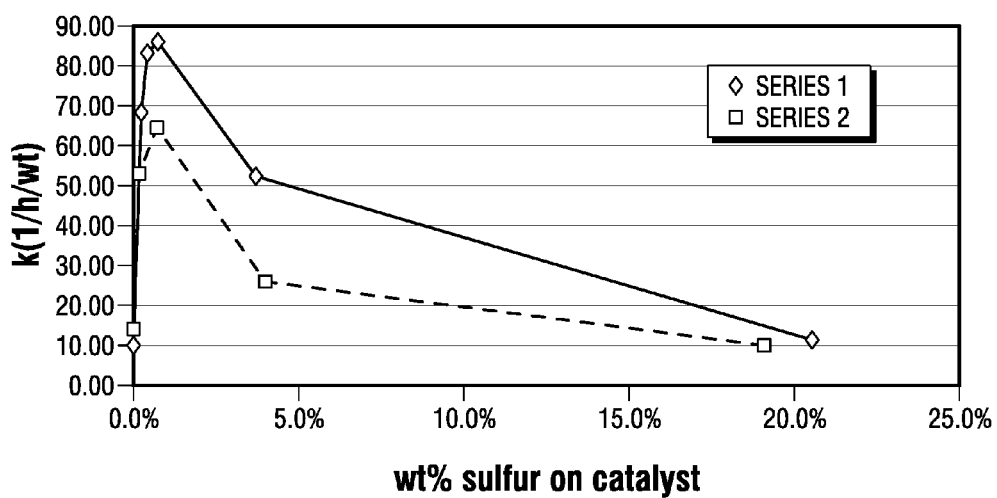
FIG. 2 is a composite graph of measured kinetic constant of a sulfided cobalt molybdenum catalyst on alumina at 240° C. in presence of water vs. sulfur concentration from the examples.

FIG. 2 shows methyl ethyl ketone hydrogenation kinetics (220° C., 52 bar $H_2$) following 48-hour stress test at 240° C. in deionized water at varying concentrations of sulfur for DMSO (series 1) and Cysteine (series 2).

We claim:

1. A method of extending the catalyst life of a hydrogenolysis catalyst activity in the presence of biomass and aqueous solution comprising: (i) providing lignocellulosic biomass solids and aqueous solution in a hydrothermal digestion unit in the presence of a digestive solvent, and a supported hydrogenolysis catalyst containing (a) sulfur, (b) Mo or W, and (c) Co, Ni or mixture thereof, incorporated into a solid metal oxide support; (ii) heating the lignocellulosic biomass solids in the hydrothermal digestion unit to a temperature in the range of 180° C. to less than 300° C. in the presence of digestive solvent, hydrogen, and in the range of 0.15 wt. % to 12.5 wt. %, based on catalyst, of $H_2S$ or $H_2S$ source at least partially soluble in aqueous solution, and the supported hydrogenolysis catalyst thereby forming a product solution containing plurality of oxygenated hydrocarbons, said hydrothermal digestion unit maintaining protective sulfur concentration.

2. The method of claim 1 wherein the residence time of the hydrothermal digestion unit (Vol/Feed) is in the range of 0.5 to 20 h.

3. The method of claim 1 wherein the $H_2S$ source comprises at least one of $SO_2$, dimethylsulfoxide, cysteine, dimethylsulfide, dimethyldisulfide, N-butylmercaptan, tertiarybutyl polysulfide, sodium sulfide, sodium thiosulfate, and di-tert-butyl polysulfide.

4. The method of claim 1 wherein $H_2S$ and/or a gaseous $H_2S$ source is added to $H_2$ stream inlet.

5. The method of claim 4 wherein $H_2S$ and/or $SO_2$ is added to $H_2$ stream inlet.

6. The method of claim 1 wherein at least a portion of the product solution is recycled to the hydrothermal digestion unit via a liquid recycle stream.

7. The method of claim 1 wherein at least one of dimethyl sulfoxide, dimethyl sulfide, dimethyldisulfide, n-butylmercaptan, teriarybutylpolysulfide, cysteine is added to the liquid recycle stream.

8. The method of claim 1 wherein further monitoring the $H_2S$ level in the gas phase in the hydrothermal digestion unit and adjusting the addition of $H_2S$ or $H_2S$ source to maintain $H_2S$ partial pressure or protective sulfur concentration in the hydrothermal digestion unit.

9. The method of claim 1 wherein $H_2S$ source is DMSO.

10. The method of claim 1 wherein $H_2S$ source is cysteine.

11. The method of claim 1 wherein $H_2S$ or $H_2S$ source or protective sulfur is recycled to the hydrothermal digestion unit.

12. The method of claim 1 wherein $H_2S$ or $H_2S$ source is present in the range of 0.15 to 10 wt. % based on catalyst.

13. The method of claim 12 wherein $H_2S$ or $H_2S$ source is present in the range of 0.15 to 5 wt. %, based on catalyst.

14. The method of claim 2 wherein $H_2S$ or $H_2S$ source or protective sulfur is recycled to the hydrothermal digestion unit.

15. The method of claim 8 wherein $H_2S$ or $H_2S$ source or protective sulfur is recycled to the hydrothermal digestion unit.

16. The method of claim 15 wherein at least a portion of the product solution is recycled to the hydrothermal digestion unit via a liquid recycle stream.

17. The method of claim 8 wherein $H_2S$ and/or a gaseous $H_2S$ source is added to $H_2$ stream inlet.

18. The method of claim 17 wherein $H_2S$ and/or $SO_2$ is added to $H_2$ stream inlet.

* * * * *